United States Patent [19]

Button et al.

[11] Patent Number: 5,492,122
[45] Date of Patent: Feb. 20, 1996

[54] MAGNETIC RESONANCE GUIDED HYPERTHERMIA

[75] Inventors: Terry Button, East Patchogue; Susan Barbour, Westbury; Justine D. Cermignani, Fort Salonga; Eric Crugnale, Port Jefferson; Robert E. McGill, Dix Hills; Glenn Spacht, Lloyd Neck, all of N.Y.

[73] Assignee: Northrop Grumman Corporation, Los Angeles, Calif.

[21] Appl. No.: 228,348

[22] Filed: Apr. 15, 1994

[51] Int. Cl.$^6$ .................................................. A61B 5/055
[52] U.S. Cl. .................. 128/653.2; 128/736; 324/315; 607/101; 607/102; 607/154; 607/156
[58] Field of Search ............................ 128/653.2, 653.5, 128/736; 607/96, 101, 102, 154, 156; 324/309, 315, 318, 322

[56] References Cited

U.S. PATENT DOCUMENTS

| | | |
|---|---|---|
| 3,919,638 | 11/1975 | Belden . |
| 4,016,886 | 4/1977 | Doss et al. . |
| 4,186,729 | 2/1980 | Harrison . |
| 4,210,152 | 7/1980 | Berry . |
| 4,228,809 | 10/1980 | Paglione . |
| 4,230,129 | 10/1980 | LeVeen . |
| 4,269,199 | 5/1981 | Armitage . |
| 4,316,453 | 2/1982 | Harrison . |
| 4,325,361 | 4/1982 | Harrison . |
| 4,350,168 | 9/1982 | Chable et al. . |
| 4,365,622 | 12/1982 | Harrison . |
| 4,378,806 | 4/1983 | Henley-Cohn . |
| 4,397,313 | 8/1983 | Vaguine . |
| 4,397,314 | 8/1983 | Vaguine . |
| 4,402,309 | 9/1983 | Harrison . |
| 4,462,412 | 7/1984 | Turner . |
| 4,554,925 | 11/1985 | Young . |
| 4,572,190 | 2/1986 | Azam et al. . |
| 4,589,423 | 5/1986 | Turner . |

(List continued on next page.)

FOREIGN PATENT DOCUMENTS

| | | |
|---|---|---|
| 0107238 | 5/1984 | European Pat. Off. . |
| 0191180 | 8/1986 | European Pat. Off. . |
| 2604890 | of 1988 | France . |
| 453533 | 2/1992 | Japan . |
| WO91/07132 | 5/1991 | WIPO . |

OTHER PUBLICATIONS

D. L. Parker et al., Medical Physics, 10:321–325 (1983).
D. LeBihan, Radiology, 171:853–857 (1989).
Delannoy et al., Magnetic Resonance in Medicine, 19:333–339 (1991).
Y. Zhang et al., International Journal of Hyperthermia, 8:263–274 (1992).
T. V. Samulski et al., International Journal of Hyperthermia, 8:819–829 (1992).

Primary Examiner—Krista M. Zele
Attorney, Agent, or Firm—Terry J. Anderson; Karl J. Hoch, Jr.

[57] ABSTRACT

A hyperthermia treatment apparatus includes an annular radio frequency (RF) antenna array with bolus that is compatible with a magnetic resonance imaging (MRI) machine. Antenna elements polarized parallel to the axis of the cylinder are used for forming a Specific Absorption Ratio (SAR) map as well as for directing the energy to accomplish hyperthermia. The array may be dynamically controlled to focus energy at any specified region within the cylinder. The array is positioned inside an MRI machine and is tuned to the machine's hydrogen resonant frequency. For treatment planning, the array is employed to form an SAR map via RF current density imaging. Using this map, array phase, amplitude, and temporal weighting are optimized until the SAR maxima is congruent with the treatment volume. For treatment, RF radiation is applied to the subject to induce heating of the treatment volume using these optimal array parameters. Temperature is periodically determined via noninvasive MRI methods (i.e., diffusion imaging, $T_1$ map, etc.) in order to obtain an image that includes isotherms from which the pattern of heating can be observed. Feedback is provided such that adjustment may be made to compensate for bioheat transfer.

19 Claims, 14 Drawing Sheets

U.S. PATENT DOCUMENTS

| | | |
|---|---|---|
| 4,617,936 | 10/1986 | Malko . |
| 4,632,127 | 12/1986 | Sterzer . |
| 4,632,128 | 12/1986 | Paglione et al. . |
| 4,638,436 | 1/1987 | Badger et al. . |
| 4,638,813 | 1/1987 | Turner . |
| 4,669,480 | 6/1987 | Hoffman . |
| 4,672,972 | 6/1987 | Berke . |
| 4,672,980 | 6/1987 | Turner . |
| 4,674,481 | 6/1987 | Boddie, Jr. et al. . |
| 4,683,813 | 8/1987 | Turner . |
| 4,707,664 | 11/1987 | Fehn et al. . |
| 4,721,913 | 1/1988 | Hyde et al. . |
| 4,721,914 | 1/1988 | Fukushima et al. . |
| 4,733,190 | 3/1988 | Dembinski . |
| 4,739,269 | 4/1988 | Kopp . |
| 4,774,468 | 9/1988 | Bydder . |
| 4,776,341 | 10/1988 | Bachus . |
| 4,784,146 | 11/1988 | Mancuso et al. . |
| 4,785,829 | 11/1988 | Convert et al. . |
| 4,791,371 | 12/1988 | Krol . |
| 4,793,356 | 12/1988 | Misic et al. . |
| 4,798,215 | 1/1989 | Turner . |
| 4,815,479 | 3/1989 | Carr . |
| 4,817,612 | 4/1989 | Akins et al. . |
| 4,819,642 | 4/1989 | Andersen et al. . |
| 4,831,330 | 5/1989 | Takahashi . |
| 4,870,363 | 9/1989 | Yassine et al. . |
| 4,875,485 | 10/1989 | Matsutani . |
| 4,891,483 | 1/1990 | Kikuchi et al. . |
| 4,897,604 | 1/1990 | Carlson et al. . |
| 4,918,388 | 4/1990 | Mehdizadeh et al. . |
| 4,920,318 | 4/1990 | Misic et al. . |
| 4,932,411 | 6/1990 | Fritschy et al. . |
| 4,934,365 | 6/1990 | Morgenthaler . |
| 4,951,688 | 8/1990 | Keren . |
| 4,960,106 | 10/1990 | Kubokawa et al. . |
| 4,968,936 | 11/1990 | Darrasse et al. . |
| 4,974,587 | 12/1990 | Turner et al. . |
| 4,978,215 | 12/1990 | Katoh et al. . |
| 4,983,159 | 1/1991 | Rand . |
| 5,007,425 | 4/1991 | Vanek et al. . |
| 5,010,897 | 4/1991 | Leveen . |
| 5,024,229 | 6/1991 | Bryant et al. . |
| 5,042,487 | 8/1991 | Marquardt . |
| 5,046,495 | 9/1991 | Takahashi et al. . |
| 5,063,933 | 11/1991 | Takahashi . |
| 5,086,786 | 2/1992 | Sogawa et al. . |
| 5,090,423 | 2/1992 | Matsuda et al. . |
| 5,097,844 | 3/1992 | Turner . |
| 5,099,756 | 3/1992 | Franconi et al. . |
| 5,101,836 | 4/1992 | Lee . |
| 5,109,853 | 5/1992 | Taicher et al. ................. 128/653.2 |
| 5,130,656 | 7/1992 | Requardt et al. . |
| 5,136,244 | 8/1992 | Jones et al. . |
| 5,139,024 | 8/1992 | Bryant et al. . |
| 5,139,474 | 8/1992 | Lamond et al. . |
| 5,143,068 | 9/1992 | Muennemann et al. . |
| 5,148,814 | 9/1992 | Kikuchi et al. . |
| 5,154,178 | 10/1992 | Shah . |
| 5,163,446 | 11/1992 | Saitoh . |
| 5,170,789 | 12/1992 | Narayan et al. . |
| 5,186,181 | 2/1993 | Franconi et al. . |
| 5,190,054 | 3/1993 | Fetter et al. . |
| 5,284,144 | 2/1994 | Delannoy et al. ................. 128/653.2 |
| 5,305,231 | 4/1994 | Kubokawa et al. . |

Tissue Properties Used in this Study

| Tissue | $\sigma$ ($\Omega^{-1} m^{-1}$) | $\epsilon_r$ | K (W/m/°C) | c × p (W·sec/m³/°C) × $10^6$ | m (ml/100g/min) |
|---|---|---|---|---|---|
| Bone | 0.020 | 10 | 0.436 | 2.25 | 0 |
| Fat | 0.220 | 10.5 | 0.210 | 2.12 | 0.03 |
| Heart | 0.930 | 89 | 0.527 | 3.72 | 84 |
| Kidney | 1.0 | 89.5 | 0.547 | 3.96 | 420 |
| Liver | 0.60 | 77.5 | 0.508 | 3.81 | 57 |
| Lung | 0.35 | 40 | 0.478 | 1.68 | 433 |
| Muscle | 0.889 | 72 | 0.642 | 3.72 | 2.7 |
| Rectum | 0.61 | 52 | 0.498 | 3.35 | 1.8 |
| Spleen | 0.78 | 100 | 0.515 | 3.81 | 60 |
| Stomach | 0.57 | 80 | 0.527 | 3.81 | 40 |
| Tumor | 0.889 | 72 | 0.640 | 3.72 | 0 |
| Viscera | 0.57 | 80 | 0.550 | 3.81 | 27 |

Note: $\sigma$ = Electrical conductivity at 100 MHz, $\epsilon_r$ = relative dielectric constant at 100 MHz, K = therm conductivity, c = specific heat, p = density, m = basal blood perfusion rate.

FIG. 2

Composition of Phantom Muscle Tissues for Various Radiofrequencies

| Frequency (MHz) | Actual Tissue (37°C) Dielectric Constant | Actual Tissue (37°C) Conductivity | Phantom Tissue (22°C) Dielectric Constant | Phantom Tissue (22°C) Conductivity | TX-150 (%) | PEP | Al | $N_2O$ | NaCl |
|---|---|---|---|---|---|---|---|---|---|
| 2450 | 47.0 | 2.17 | 47.4 ± 0.9 | 2.17 ± 0.08 | 8.46 | 15.01 | — | 75.48 | 1.051 |
| 915 | 51.0 | 1.28 | 51.1 ± 0.6 | 1.27 ± 0.02 | 8.42 | 15.44 | — | 75.15 | 0.996 |
| 750 | 52.0 | 1.25 | 52.5 ± 0.6 | 1.26 ± 0.04 | 8.42 | 15.44 | — | 75.15 | 0.996 |
| 433 | 53.0 | 1.18 | 53.5 ± 0.5 | 1.21 ± 0.01 | 8.42 | 15.44 | — | 75.15 | 0.996 |
| 300 | 54.0 | 1.15 | 54.8 ± 0.7 | 1.17 ± 0.01 | 8.42 | 15.44 | — | 75.15 | 0.996 |
| 200 | 56.5 | 1.00 | 56.7 ± 0.7 | 1.06 ± 0.02 | 8.39 | 15.79 | — | 74.92 | 0.894 |
| 100 | 71.7 | 0.89 | 71.5 ± 1.1 | 0.89 ± 0.01 | 9.81 | — | 2.12 | 87.59 | 0.462 |
| 70 | 84.0 | 0.79 | 84.7 ± 0.5 | 0.76 ± 0.01 | 10.36 | — | 2.72 | 86.50 | 0.424 |
| 40.68 | 97.0 | 0.68 | 97.9 ± 3.8 | 0.70 ± 0.02 | 9.68 | — | 9.20 | 80.82 | 0.303 |
| 27.12 | 113.0 | 0.60 | 113.0 ± 3.0 | 0.62 ± 0.02 | 9.70 | — | 9.06 | 80.97 | 0.270 |
| 13.56 | 149.0 | 0.62 | 149.0 ± 3.0 | 0.62 ± 0.03 | 9.69 | — | 9.15 | 80.88 | 0.280 |

From Chou et al[8]

FIG. 3

MAGNETIC RESONANCE GUIDED HYPERTHERMIA

BACKGROUND OF THE INVENTION

Field of the Invention

This invention relates to a hyperthermia treatment apparatus and method, and more particularly to a hyperthermia treatment apparatus and method which utilizes a cylindrical phased array of axially polarized antennas and a magnetic resonance imaging (MRI) machine.

Description of Related Art

The use of elevated temperatures, i.e., hyperthermia, has been employed for some time and is becoming a recognized form of cancer therapy, particularly when used as an adjunct to other modalities such as radiotherapy and chemotherapy. The goal of hyperthermia treatment is the destruction of tumors by raising their temperatures for an extended period of time. When certain cancerous tumors are treated by raising the temperature of the tumor to approximately 43° C. for periods of 30–60 minutes via the process of hyperthermia, those tumors have been shown to be more susceptible to the effects of radiation and chemotherapy. The treatment relies on the primitive nature of tumor vasculature: tumor vasculature is less able than the vasculature of normal tissues to vasodilate in response to thermal stress. A thermal stress, as is induced in the hyperthermia process, consequently raises tumor temperature more than that of surrounding normal tissue because the vasculature cannot carry away the heat efficiently. If tissue temperature remains elevated for an extended period of time, DNA synthesis is reduced, cell respiration is depressed, irreversible destruction of structure (and thus function) of chromosome associated proteins can occur, and autodigestion by the cell's digestive mechanism can result. Extended periods of elevated temperature can also sensitize cells to radiation and/or chemotherapeutic drugs.

A variety of methods have been employed in the past for inducing hyperthermia. Various applicators have been designed to deliver energy, typically ultrasound or electromagnetic energy, to a localized target area. Applicators for superficial tissue heating are relatively easy to monitor and control. In the case of electromagnetic applicators, microwaves have been employed for treatment close to the skin surface. For deep treatment, electromagnetic applicators must either be invasive or must operate in the lower, radio frequency (RF), band of the spectrum to achieve penetration deeper into the body. Treatment planning for deep hyperthermia must also rely on image information available to the physician. The best sources of three dimensional (3-D) spatial image data are computerized tomography (CT) and magnetic resonance imaging (MRI). In U.S. Pat. No. 4,554,925, Young presents a Magnetic Resonance Imaging-(MRI) apparatus that is connected to a hyperthermia means for the purpose of localizing tumor volume in a patient.

Although the bioheat transfer mechanism in the body permits healthy tissue to regulate its temperature more efficiently than tumor tissue, in order for the hyperthermia process to be safe and effective, the heating during a hyperthermia procedure must be localized in the tumor volume to the maximum extent possible, and must also be uniform across that tumor volume. Particularly in the cases where hyperthermia is used as an adjunct to radiation therapy and chemotherapy, significant hyperthermia to adjacent normal structures should be avoided to prevent hypersensitizing the healthy tissue to radiation and/or drugs. It is also essential that the heating be almost uniform within the tumor volume being treated. Relative cool spots during treatment may result in failure to kill certain cells, and perhaps the selection of cells with thermal tolerance (i.e., resistant to future hyperthermia treatment). The ideal power distribution for hyperthermia, therefore, is a pattern that provides broad, uniform heating over the entire treatment volume, with a rather sharp drop-off at the tumor margins.

During a hyperthermia procedure, careful monitoring of tissue temperature is required, both within the tumor and in the surrounding healthy tissue. Measurement of tissue temperature has, in the past, relied upon invasive techniques, primarily temperature sensing probes inserted in the patient. However, beyond the basic safety concerns associated with the use of invasive probes, this technique provides only selected temperature data points, limited by the number of probes that can be inserted into the patient. Furthermore, the complexity associated with accurately locating invasive temperature probes during hyperthermia increases in proportion to the depth of the treatment. Even with well located probes, for deep hyperthermia the ability to monitor temperature uniformity across the tumor volume and in the healthy surrounding tissue is difficult at best.

Driven by the desire of those skilled in the art for a non-invasive temperature monitoring method to support hyperthermia, a significant body of research exists demonstrating the use of MR imaging to noninvasively measure temperature to a resolution of better than $0.5°$ C./cm$^3$. As MR imaging speed has increased, the time to obtain an MR diffusion image of temperature has dropped from minutes to seconds. The following references relate to the use of MRI for temperature measurement: D. L. Parker et al, Medical Physics, 10: 321–325 (1983); D. Le Bihan et al, Radiology, 171: 853–857 (1989); Delannoy et al, Magnetic Resonance in Medicine, 19: 333–339 (1991); Y. Zhang et al, International Journal of Hyperthermia, 8: 263–274 (1992); T. V. Samulski et al, International Journal of Hyperthermia, 8: 819–829 (1992).

The non-invasive RF hyperthermia applicators that have been employed in the past for deep treatment within a patient have suffered from inadequate control of the power distribution into the patient. The initial enthusiasm for findings concerning the ability of hyperthermia to destroy tumors without being mutagenic, myelo-suppressive, or compromised by other methods of therapy, has been tempered by the inability to deliver a well-controlled deep thermal dose. Inadequate control of power for these deep treatment applicators in the past has been attributed to several factors:

(1) The longer RF wavelengths required for deep tissue penetration are more difficult to focus on a small target area.

(2) Inhomogeneous electrical characteristics of patient tissue results in attenuation, phase shifting, reflection, and refraction of the electromagnetic radiation.

(3) The inability to measure the Specific Absorption Ratio (SAR) map of power into the patient, and use that information to optimize the treatment for a specific patient; this inability to actually measure RF power into the patient has resulted in the development of complex models to approximate the initial conditions to achieve a desired SAR.

(4) The inadequacy of beam-shaping techniques to flexibly accommodate a variety of tumor sizes and shapes.

(5) The limitation of temperature measurement to invasive methods that result in an incomplete 3-D rendering of actual resulting temperature profile during a hyperthermia procedure.

Several devices have been proposed for deep hyperthermia treatment. For example, one previously disclosed RF hyperthermia device is an annular phased array (APA) described by Turner, IEEE Transactions, BME, 31: 106–114 (1984). In the Turner apparatus, eight apertures are arranged in a cylindrical configuration with tunable operating frequencies of between 50 and 110 MHz to provide an electric field that is polarized along the cylinder axis. Theoretical distributions and clinical evaluations for this device have, however proven disappointing. In addition to the Turner system, cylindrical phased arrays for regional hyperthermia have been disclosed in U.S. Pat. Nos. 4,978,215, 4,638,813, and 5,097,844, in Paulsen et al, Radiation Research, 100: 536–552 (1984), and in Morita et al, Bioelectromagnetics, 3: 253–261. The use of a cylindrical phased array for combining regional hyperthermia and microwave detection (radiometry) to noninvasively measure temperature distributions during treatment is disclosed in U.S. Pat. No. 4,815,479. Keren's U.S. Pat. No. 4,951,688 proposes an RF hyperthermia array used in conjunction with MRI that includes a technique to determine an initial phase and amplitude setting to steer the array. In International Patent Disclosure No. WO 91/07132 filed by Delannoy et al, a hyperthermia treatment system is proposed, in various embodiments, that utilizes the capability of MRI to noninvasively evaluate tissue temperature; a 3-D temperature profile provided by the MR imager is utilized as feedback to the hyperthermia applicator during treatment.

Unfortunately, none of these prior hyperthermia array inventions adequately address all of the problems associated with noninvasive, deep hyperthermia treatment. While all are able to accomplish power localization to various degrees, none have successfully been able to accommodate the inhomogeneity effects of the body. Dosimetry for these devices has been roughly equated to temperature measurement. In order to optimize the distribution characteristics of an array, however, precise knowledge of the field is required. Treatment planning based solely on analytic techniques can not accurately account for the inhomogeneities found within a patient. Planning based solely on preliminary temperature maps can not account for heat removal through biological transfer nor can array parameters be adequately optimized. Direct noninvasive mapping of the field is the most precise method for plan optimization but has, until now, not been possible.

Noninvasive temperature measurement does remain an essential element in a hyperthermia system for deep treatment, primarily as a monitoring and feedback mechanism to ensure procedural effectiveness and to monitor patient safety; it is essential to know that uniform heating is occurring in the target area, and stray heating is not occurring in other areas. However, mapping the field to yield an SAR map based on noninvasive measurement within the patient is a deficiency in the prior inventions. The prior five inventions are also deficient in providing dynamic power control to accommodate the broad range of tumor geometries that can exist, control that can be provided by complex beam shaping techniques and time-averaging algorithms applied in addition to basic phase and amplitude control in an array. In essence, all lack the ability to a priori map the actual SAR and then optimize the array control based on that SAR. These are design elements that are essential for successful control of the power to the tumor volume.

The present invention, as will be apparent from the following description, differs from the above noted art in that it will combine a steerable cylindrical phased array of axially polarized antennas and an MRI machine, but further incorporates techniques to rapidly and noninvasively provide a 3-D temperature map, techniques to measure and map the SAR in the patient for optimization of RF power dosimetry, and techniques to accomplish static and dynamic control of the power delivery to the patient.

SUMMARY OF THE INVENTION

It is accordingly a principal objective of the invention to provide a method and apparatus for hyperthermia treatment which is capable of providing a measured deep thermal dose to a specified treatment volume which when used with other therapies should cause tumor destruction, while sparing normal tissues.

In order to accomplish this principal objective, it is also an objective of the invention to provide a method and apparatus for controlling power distribution and measuring tissue temperatures capable of controlling and raising tumor temperatures to approximately 43° C. for 30–60 minutes, while allowing surrounding normal tissue to remain below 42° C.

It is a further objective of the invention to provide a method and apparatus for optimizing the distributed power delivery during hyperthermia treatment. The power can be varied and controlled within the patient based on noninvasive near real time monitoring of tissue temperatures.

It is yet another objective of the invention to provide a hyperthermia treatment system in which heating and monitoring are performed at the same frequency, and in which a visual display of the measured SAR distribution is provided rather than a theoretically based SAR.

It is yet another objective of the invention to provide an array of axially aligned antennas that allows for temporal averaging for shaping of the field to improve the SAR distribution such that tumor coverage is optimum while normal tissue heating is minimized.

It is yet another objective of the invention to provide noninvasive monitoring of tissue temperature so that tumor is heated to a therapeutic temperature while normal tissue is not.

In accordance with the principles of the preferred embodiment of the invention, simultaneous use is made of an MRI machine and a cylindrical phased array of antenna elements, positioned within the MRI machine. These antenna elements each have separate phase and amplitude controls and can be employed in a pulsed or continuous mode. This combination of what is essentially a clinical MR imager with a complex phased array of RF elements is referred to herein by the term magnetic resonance guided hyperthermia (MRGHT). The array, like the basic MRI equipment, is tuned to the hydrogen magnetic resonance frequency. The combination of an RF array and an MRI machine in the preferred embodiment allows the array to provide RF pulses causing current densities within the patient which result in transverse magnetic fields which are detected by the MR imager for the purpose of image formation. Through appropriate sampling, it is possible to directly form an image of the current density generated by the array within the patient and therefore the SAR. The array also serves the purpose of delivering energy to heat the tumor volume. The MRI system performs dosimetry to measure localized temperatures in the region of the tumor during treatment. Preferably, axially aligned and polarized antenna elements are used; providing optimized RF penetration, less subcutaneous fat heating, and a proper configuration to provide axial current densities necessary for MR image formation.

A preferred method of performing an MRGHT treatment involves placement of the patient in a bolus/treatment array and positioning the patient containing bolus/treatment array in the MRI machine. A conventional hydrogen MR image is formed. This provides an accurate determination and localization of tumor volume. Current density images are then acquired using a selected set of phases and amplitudes to the antenna array and an SAR map formed. The SAR map is then superimposed upon the conventional hydrogen MR image and the congruency of the peak RF power and the treatment volume is visually evaluated. If the phase and amplitude set employed does not provide correct coverage of the tumor geometry, then these variables of each element in the array are adjusted until acceptable coverage of the tumor is provided. One method of determining optimum array setting involves collecting current density images from each array element. Array optimization routines will then be used to calculate array element amplitude, phase and temporal weighting for each patient.

Once the array is tuned with optimized phases, amplitudes and weighting, the tumor can be heated at high power using either a continuous or pulsed mode. The therapy is periodically interrupted to make a full or partial MR diffusion image to assess treatment progress. Since diffusion is dependent upon temperature, thermal dosimetry may be directly and noninvasively assessed in all tissues from this image, to an accuracy of approximately 0.2° C. Such thermal dosimetry allows adjustments in the treatment to be facilitated if normal tissues overheat or if the tumor is insufficiently heated.

BRIEF DESCRIPTION OF THE DRAWINGS

FIG. 2 is a table listing tissue properties.

FIG. 3 is a table listing compositions of phantom muscle tissues for various radio frequencies.

DETAILED DESCRIPTION OF THE PREFERRED EMBODIMENTS

Figure 1:
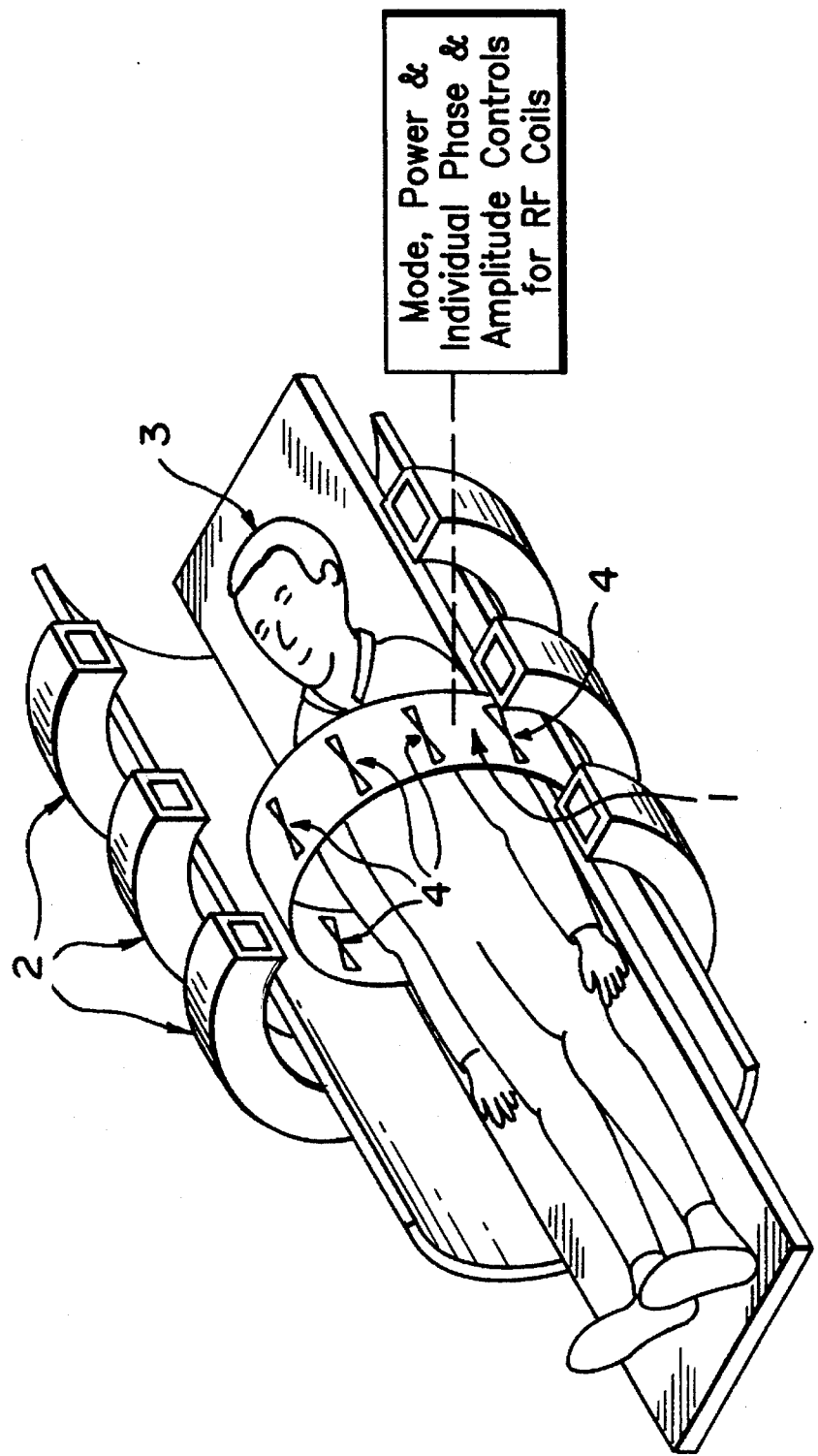
FIG. 1 is a partial cut-away perspective view of an MRI machine with a cylindrical phased array of axially aligned antennas arranged in accordance with the principles of a preferred embodiment of the invention.

FIG. 1 illustrates the basic environment in which the invention is used. The antenna array (1) within the MR imager (2) may be separated from the patient (3) using a bolus (not shown) filled with media having low conductivity/paramagnetic solution. This bolus serves to improve coupling, minimize stray and capacitive fields, minimize high spatial frequency components which are rapidly attenuated and which otherwise may result in superficial heating, and also to cool the patient's surface to minimize problems associated with systemic heating. In accordance with the invention, the antenna elements (4) which make up array (1) are preferably employable in either a pulsed or continuous mode, and at variable power levels. The complex array is most efficient if the antennas (4) are axially aligned in order to achieve best RF penetration, less subcutaneous fat heating, and to detect and or excite (through the creation of current densities within the patient) in the MR image formation.

A well investigated approach for noninvasively treating deep seated lesions using hyperthermia involves the utilization of a cylindrical phased array which surrounds the patient and is fed with an amplitude and phase distribution to localize RF energy within the patient at any specified internal location. To date, the degree of success in this approach has been limited by the following physical phenomena:

(1) The dielectric properties of a human are generally lossy as can be seen in the second column of the table shown in FIG. 2 (measured at a frequency of 100 MHz).

Figure 4:
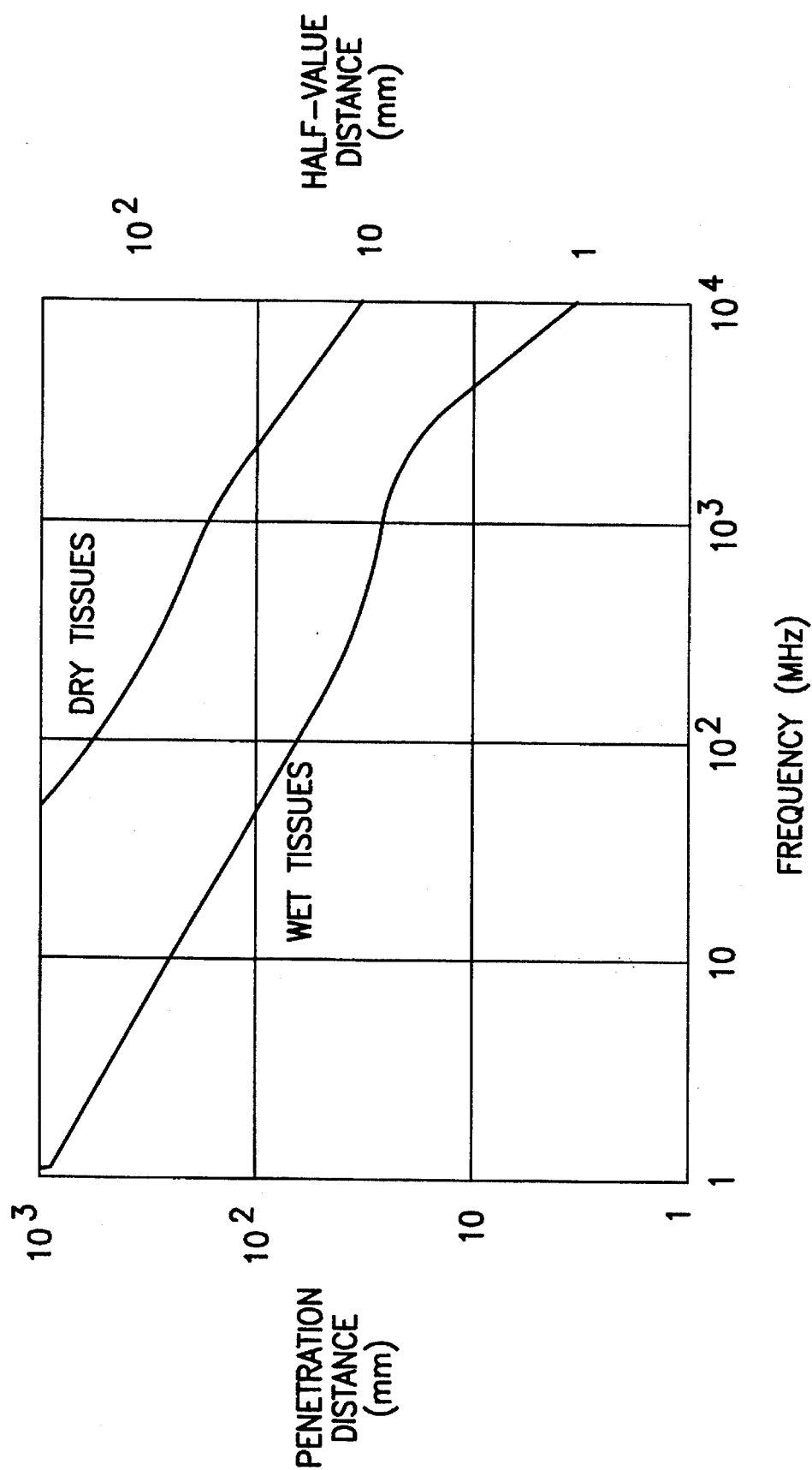
FIG. 4 is a graphical depiction of plane wave penetration into tissues with high and low water content as a function of frequency.
Figure 5:
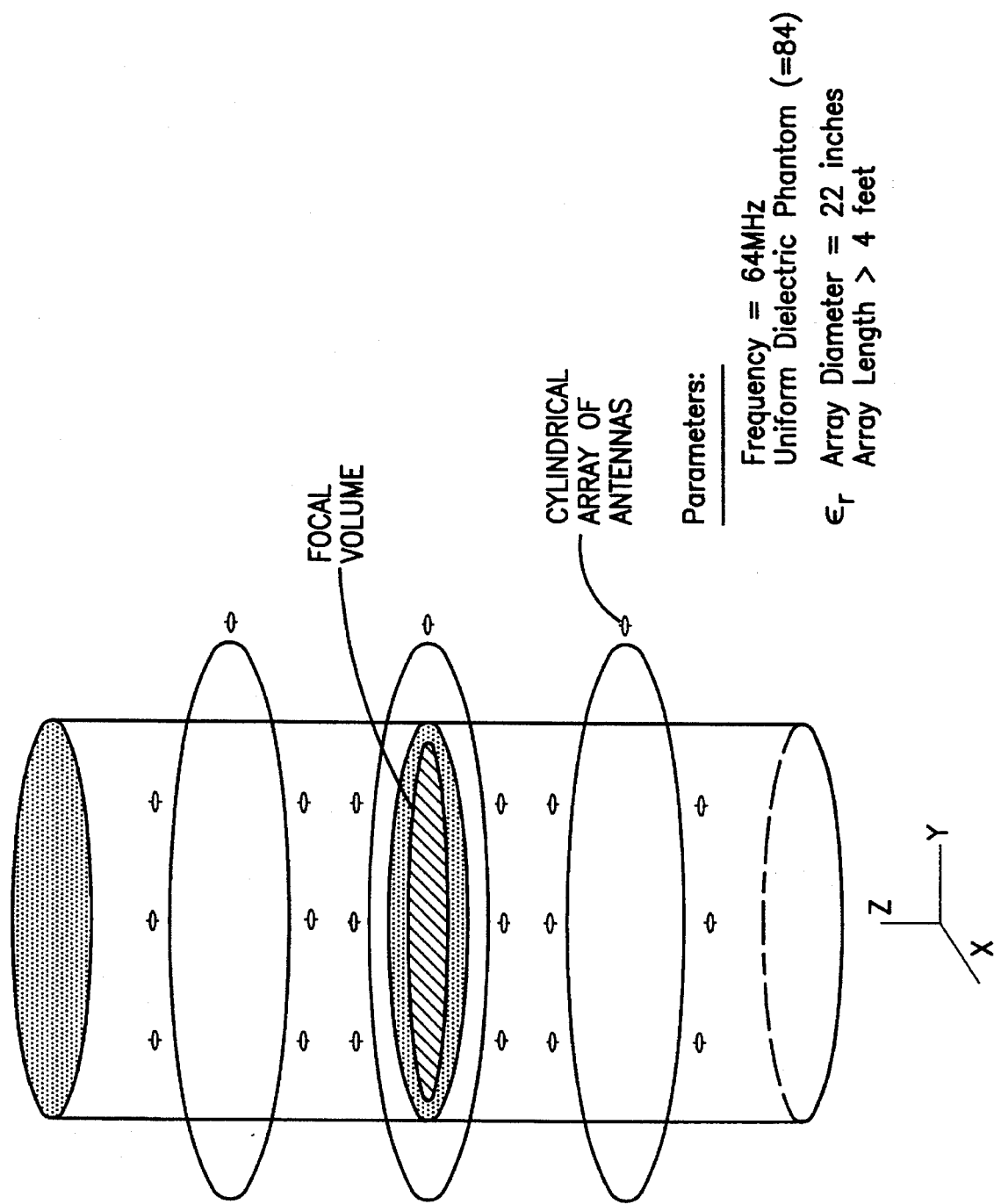
FIG. 5 is a diagram depicting the localization of RF power from a conventional phase and amplitude focusing of a three ring array.

(2) The lossy nature of tissue increases with frequency as shown in FIG. 4 and in the table of FIG. 3.

The second feature forces the design of deep heating electromagnetic devices toward lower operating frequencies to achieve adequate penetration. Unfortunately, lower frequencies do not focus RF energy sharply unless large apertures are available. Higher frequencies require more antenna input power which is dissipated almost entirely prior to reaching the desired focal point inside the patient because of the high exponential amplitude taper of the propagating wave brought about by the high loss factor. The design must therefore balance the selection of operating frequency on penetration provided by low frequency and focusing provided at high frequency.

A near-field electronic scanning mode is introduced to the antenna array which tilts and/or rotates the quiescent RF field within the patient about a focal point (treatment volume). Time integration of the ensemble of the resulting field distributions significantly improve the fall off rate of the desired focused energy near the focal point without having to increase the operating frequency.

The temporal averaging technique presumes that the cylindrical array dimensions are compatible with the inside bore opening of an MRI machine so that such an array could be physically integrated within an MRI machine to operate in a time sharing mode between RF hyperthermia and temperature monitoring using diffusion MR. We assume that the desired focal point is at the center of the cylinder containing the antenna array for the purposes of this discussion, however, those skilled in the art will appreciate that focus of RF energy may be steered adaptively to any focal point region within the cylinder.

Figure 6C:
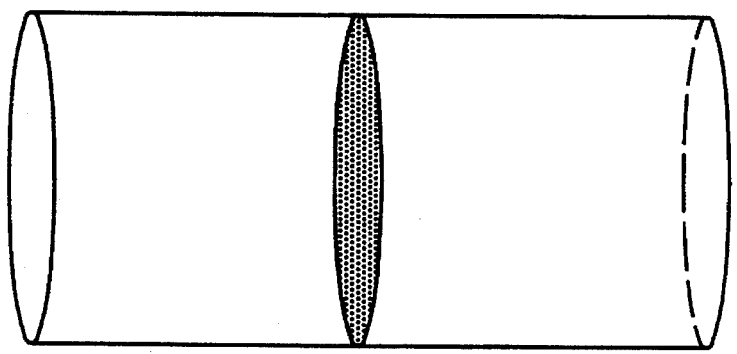
FIGS. 6a–6c are diagrams depicting time averaged RF localization from tilted fields in accordance with a preferred embodiment of the invention.
Figure 6B:
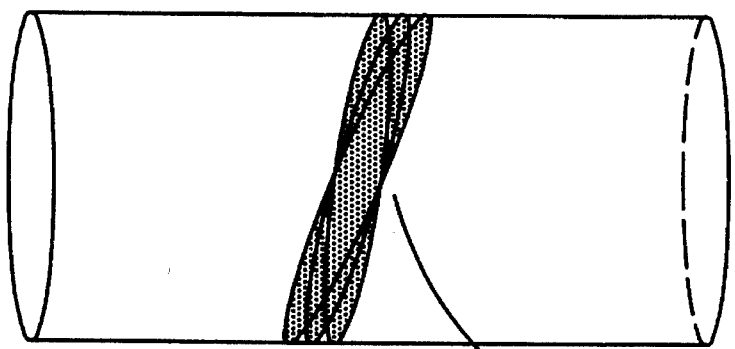
Figure 6A:
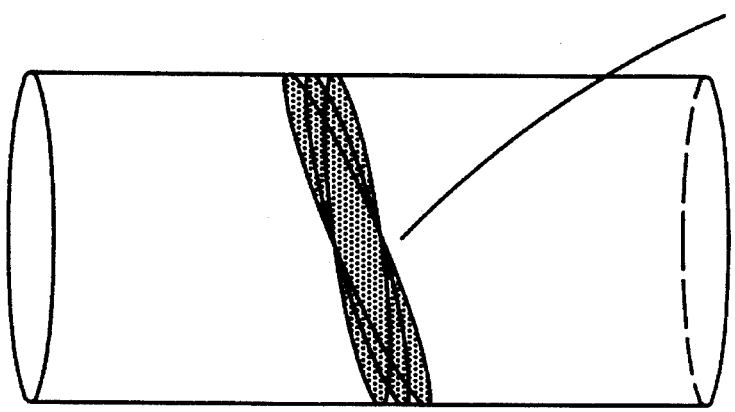

The aperture along the length of the cylinder is maximized by utilizing multiple antenna ring arrays stacked along the axis of the cylinder to provide a sharply focused field in the axial direction. The elements in each ring are individually fed with a uniform phase and amplitude distribution to focus the field on the axis of the cylinder while a suitable phase taper between the rings is selected to further focus the field at the center of the cylinder. Since the diameter of the cylinder is less than its length, focusing in the transverse plane is not as sharp as in the axial direction (See FIG. 8). An additional amplitude and phase taper superimposed upon the quiescent aperture distribution to create a virtual cylindrical array tilted about a radial axis passing through the focal point causes the focused field to tilt accordingly with minimal distortion. After repeating this process for M radial axes passing through the focal point, the absorption rate density (ARD) may be determined from the electric field (E) form each of the M orientations as follows (See FIGS. 6a and 6b):

$$ARD(\underline{r}) = \sigma/2 \frac{\sum_{i=1}^{M} |E_i(\underline{r})|^2 \delta t}{M\delta(t)} \approx \sigma/2 \frac{\int_0^T |E_i(\underline{r},t)|^2 dt}{\int_0^T dt}$$

The absorption rate density ARD($\underline{r}$) is proportional to the initial heating rate which will be focused more sharply in the transverse E plane, since the above summation remains stationary in time at only one coordinate, namely, at the original focal point where the local E field maximum resides. At all other coordinates, the highly eccentric tilting ellipsoidal focal volume causes the corresponding E($\underline{r}$) contributions to diminish, hence, focusing is improved (See FIG. 6c).

Figure 7:
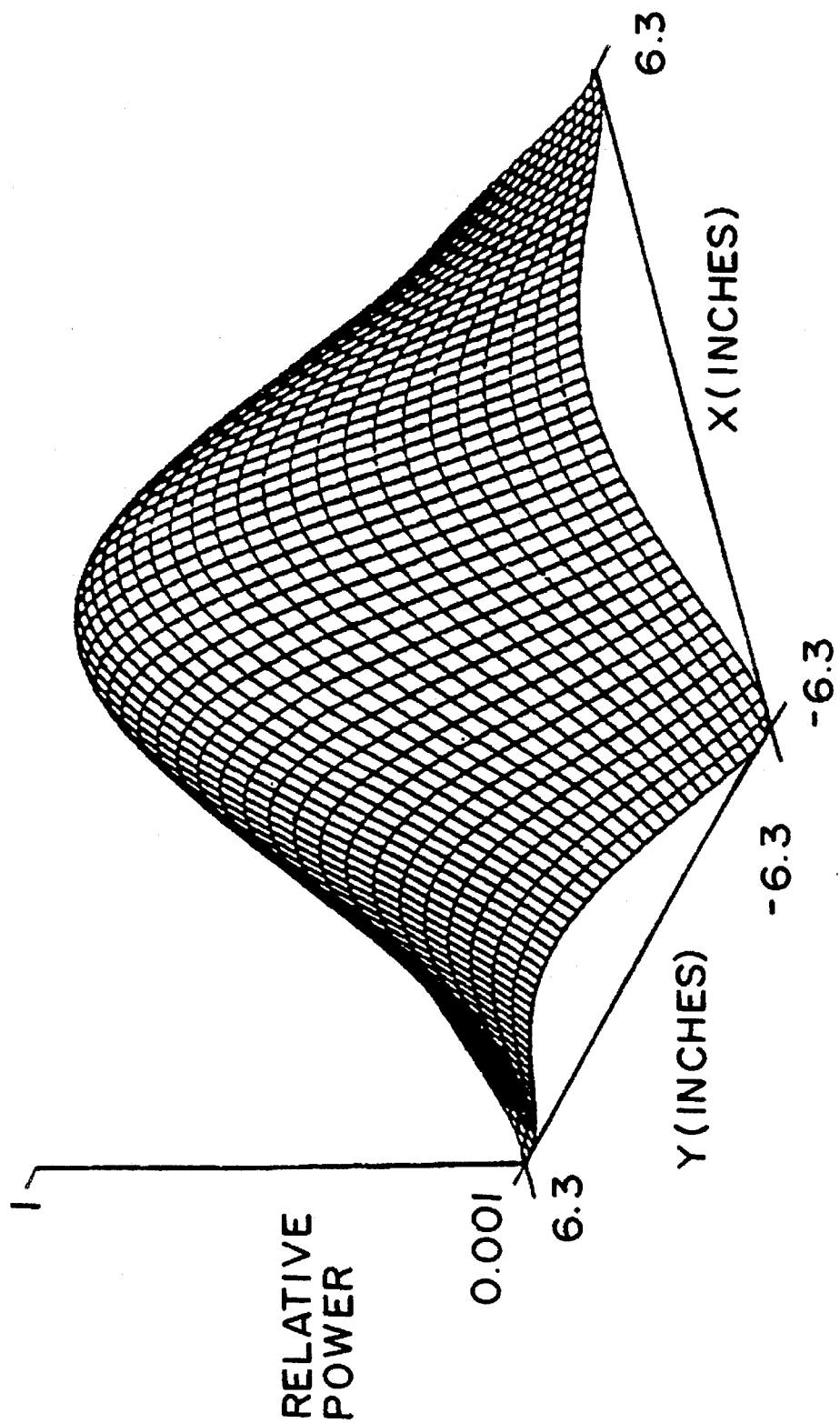
FIG. 7 is a graphic depicting RF power distribution in the transverse plane using conventional focusing in a uniform, no loss media.
Figure 8:
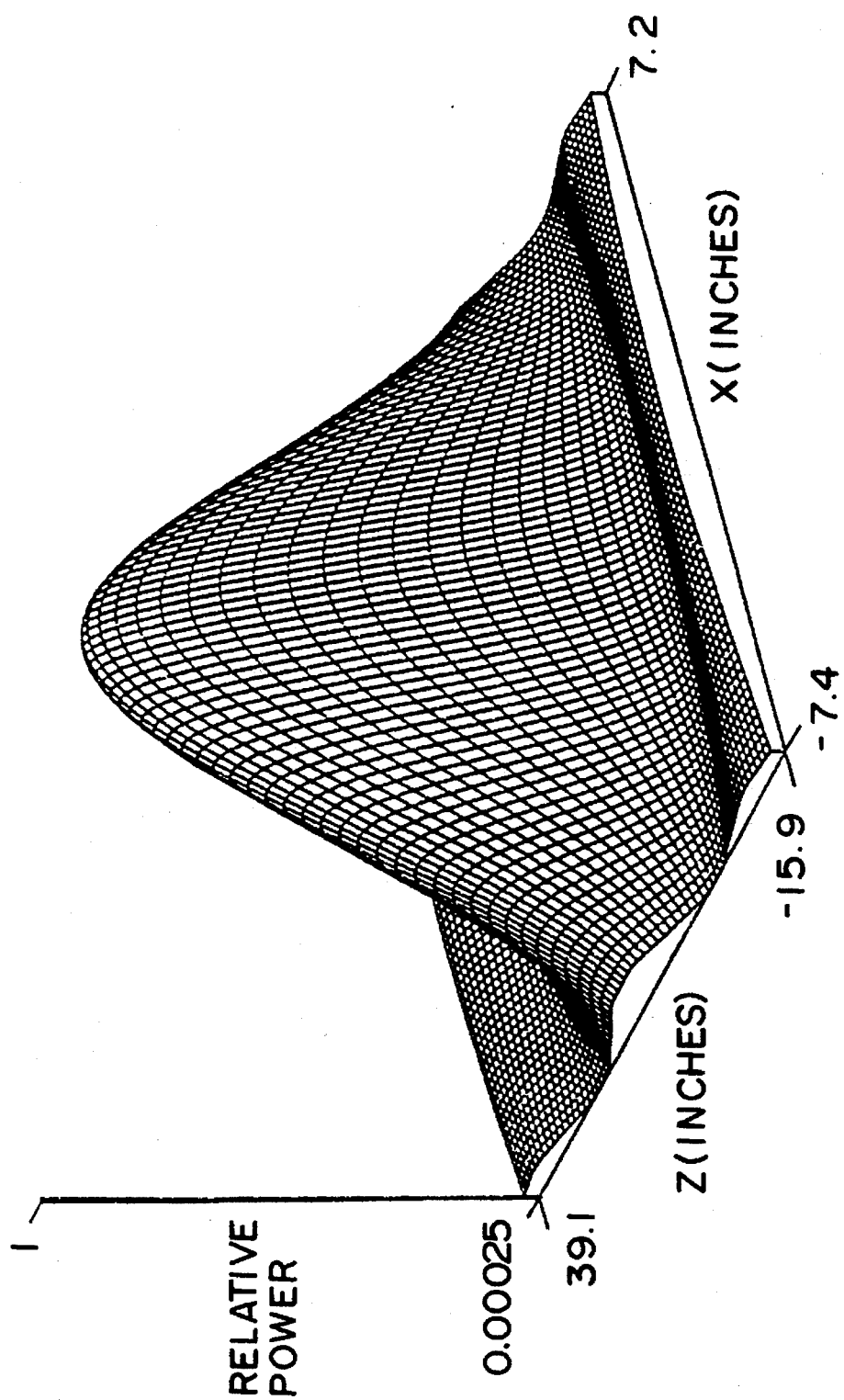
FIG. 8 is a graphic depicting RF power distribution in the longitudinal plane using conventional focusing in a uniform, no loss media.
Figure 9:
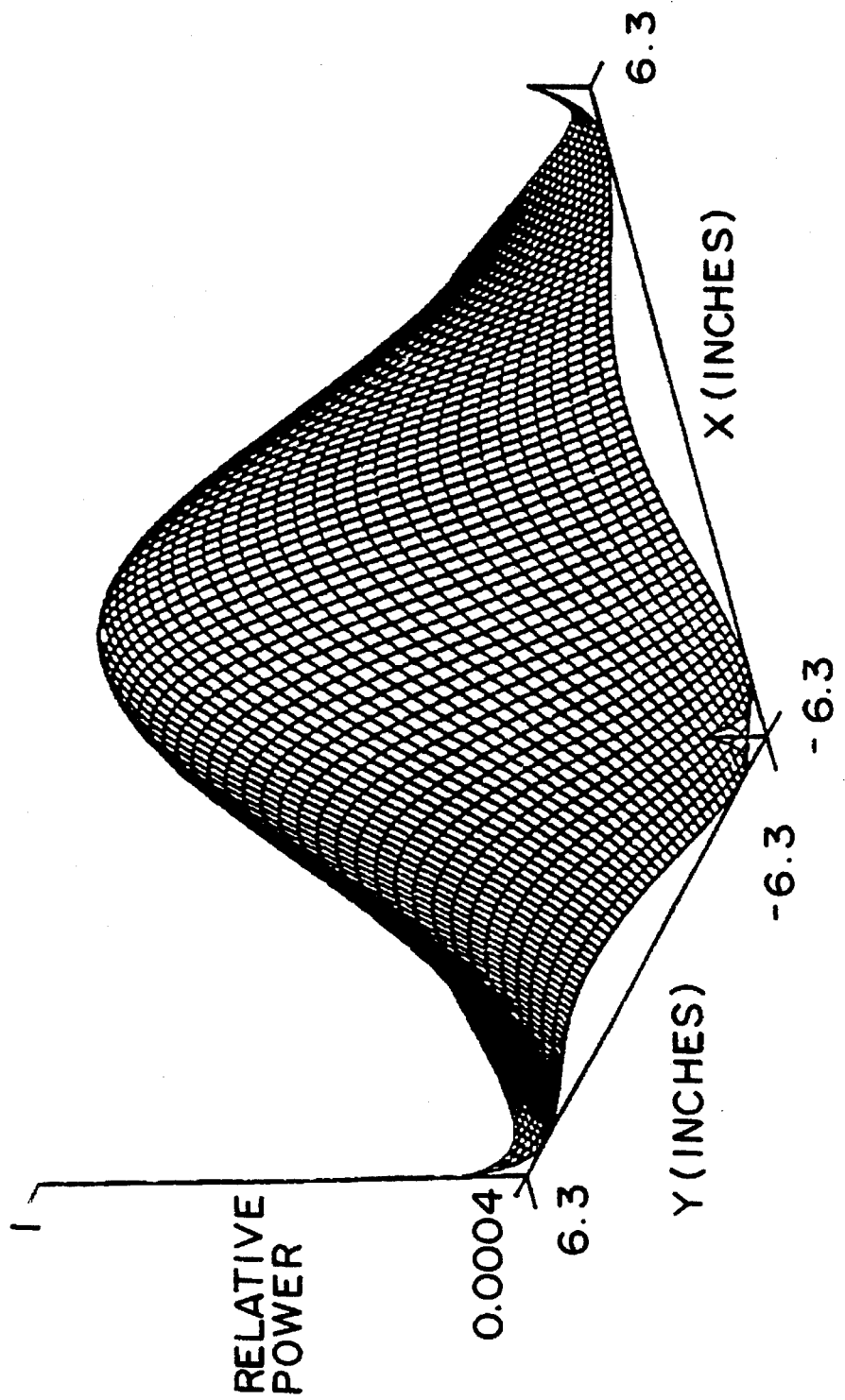
FIG. 9 is a graphic depicting RF power distribution in the transverse plane using time averaged tilted field focusing in a uniform, no loss media.
Figure 10:
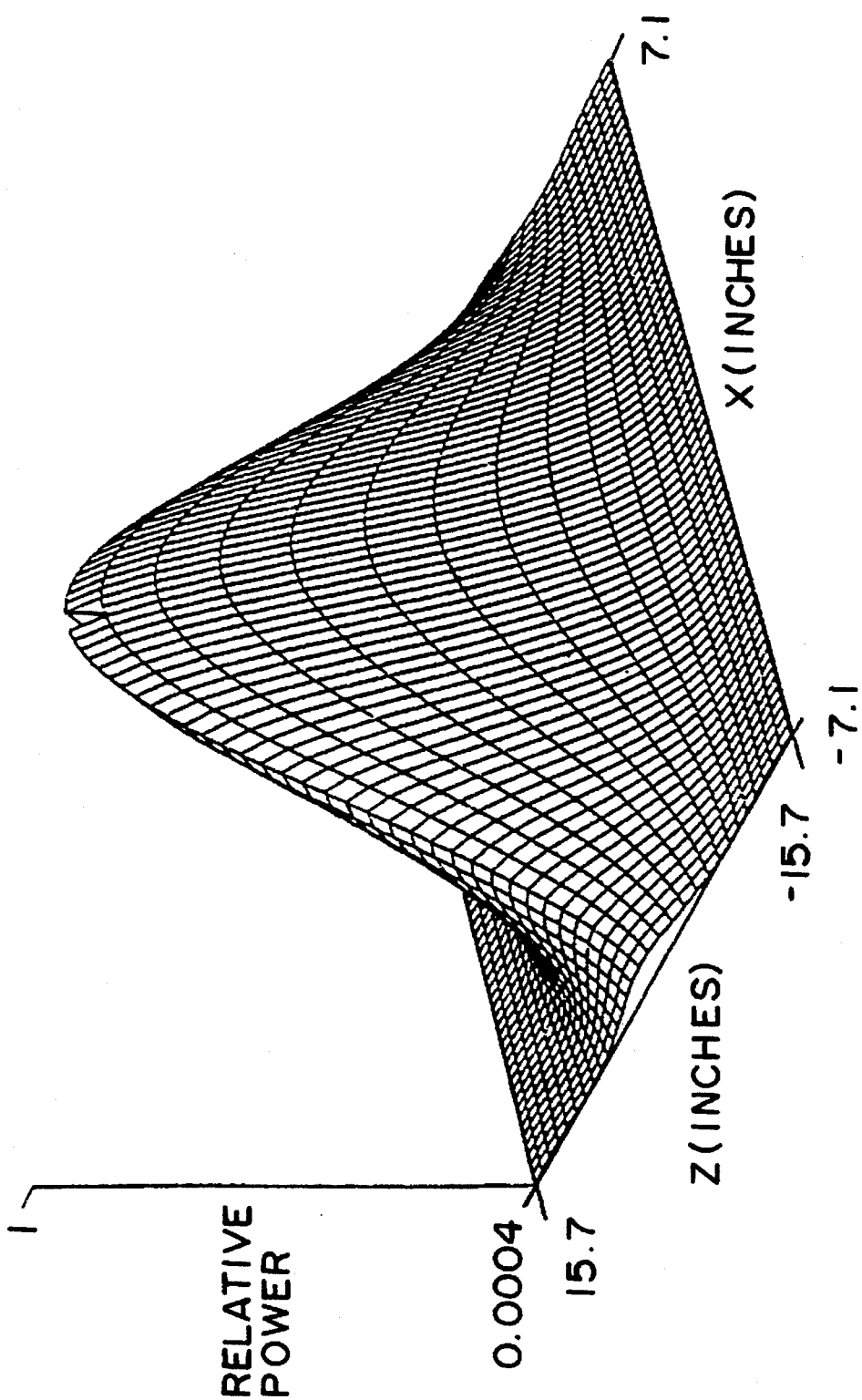
FIG. 10 is a graphic depicting RF power distribution in the longitudinal plane using time averaged tilted field focusing in a uniform, no loss media.
Figure 11:
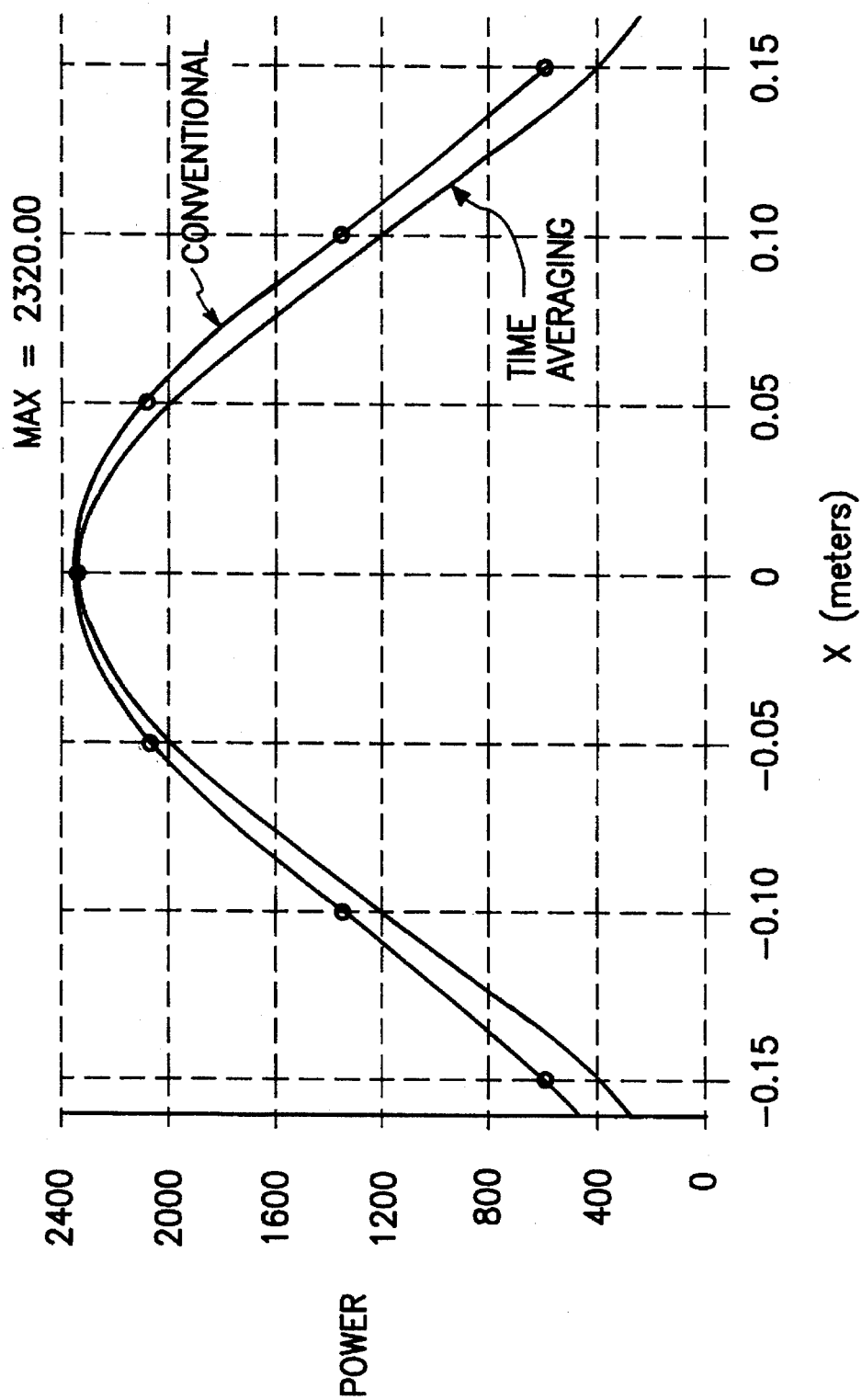
FIG. 11 is a graph comparing conventional vs. time averaged focusing.

Computer simulated results are presented in FIGS. 7 through 9 for a cylindrical array with a diameter of 22 inches having 16 rings with 8 elements per ring and an operating frequency of 64 MHz. FIGS. 7 and 8 represent the power density distributions in the transverse and longitudinal planes of the cylinder using a conventional focusing approach (uniform amplitude and phase). FIGS. 9 and 10 represent the resulting power density distribution after time averaging using 24 electronically scanned tilted field distributions. An improvement in the focusing of RF energy in the transverse plane is noted (See FIG. 11).

The antenna elements (4) in the array (1) of FIG. 1 are in the form of RF antenna elements that are both phase and amplitude controlled through multiple source apertures in a manner which will be easily implemented by one skilled in the art.

Figure 12:
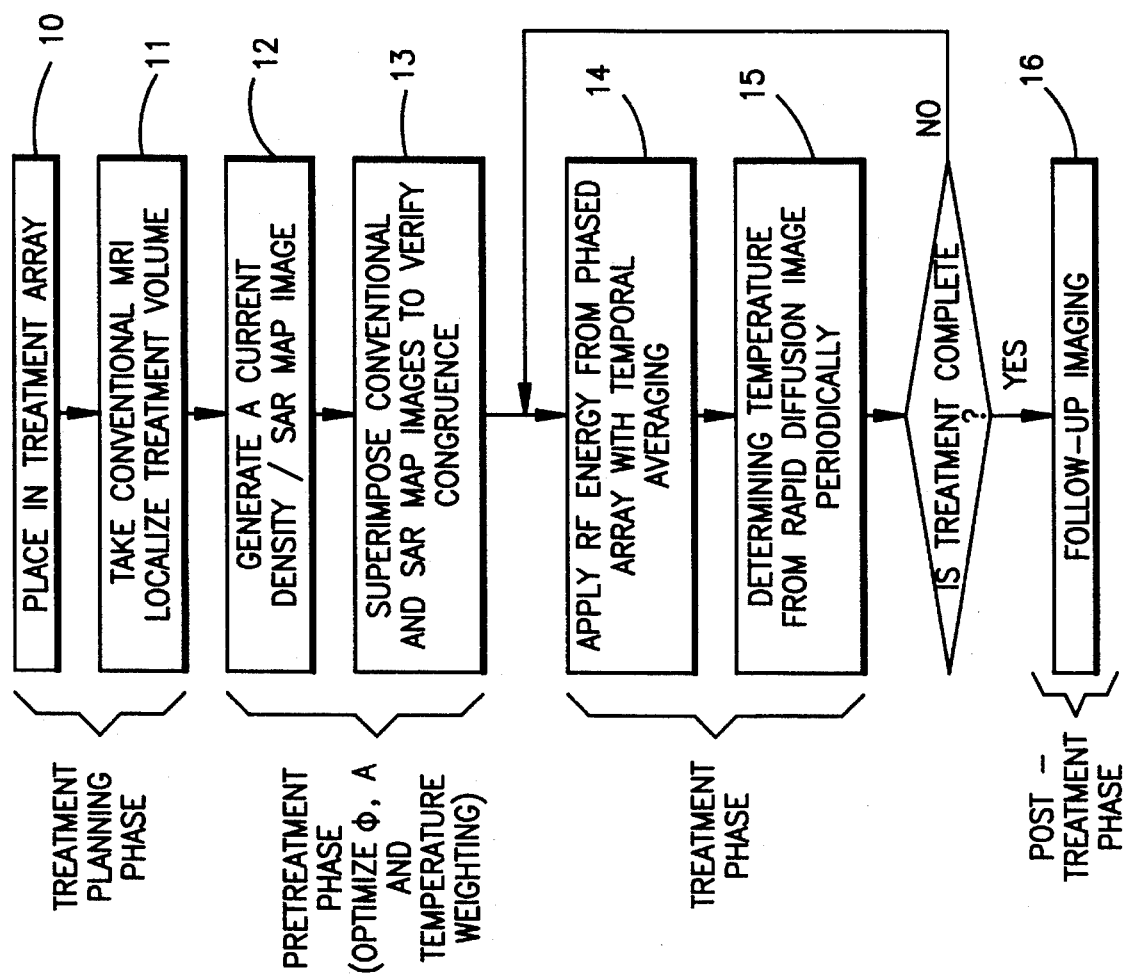
FIG. 12 is a flow chart illustrating a preferred method of practicing the invention.

As shown in FIG. 12, in order to employ this apparatus for hyperthermia treatment, after placement of the patient in a bolus/treatment array and positioning the patient in the MRI machine (step 10), a conventional hydrogen MR image is made (step 11) using the usual clinical imaging RF coils (not shown) provided in the MRI machine, with the heating antenna array (1) in place but decoupled. Alternatively, the heating array may contain switching capability such that during image formation the array behaves as a modified birdcage imaging coil and during heating it behaves as an array of axially aligned antenna elements.

These initial images allow for accurate localization of tumor volume as well as the determination of tissue signal intensity prior to diffusion attenuation as is used in noninvasive temperature mapping. These images can likewise be used with analytical models to compute the initial transmission phase and amplitude of each element in the array to achieve maximum RF power deposition within the lesion.

The SAR that results within the patient may be constructed by using the hyperthermia array as a transmitter in the MR imaging sequence. This aspect of hyperthermic treatment planning is accomplished through the noninvasive measurement of current density within the body. Using the axial arrangement of antenna tuned to the resonant (Larmor) frequency transmitting with the amplitude and phase sets under evaluation result in an electric field and therefore a current density (J) which is predominantly along the axis (z) of the array. These currents results in a magnetic field (B) having components in a plane perpendicular to this axis at the Larmor frequency. Using magnetic resonance imaging and through appropriate sampling strategies, the field (B) may be reconstructed at every point (voxel). Using Ampere's Law $$\left( \bar{J} = \frac{1}{\mu_0} \nabla \times \bar{B} \right)$$

the current density (and its relative phase) at every point may likewise be determined. Since the total current density ($J_t$) is the sum of each component and SAR=$|J_t|^2/(\sigma\rho)$, (where $\sigma$ is the tissue conductivity and $\rho$ is the density), an empirical map of SAR is therefore provided.

It should be noted that temperature-based SAR maps may be formed using diffusion MRI techniques but provide no time dependence of the field and therefore no information for array optimization. The approach using current density imaging provides the information on element field interactions needed to accomplish optimization.

One method for determining the optimal array element amplitude and phase for a patient configuration may involve analytical methods whose results are tested as described above. The SAR distribution may then be superimposed upon the conventional MR image to compare the congruency of peak RF power and treatment volume (step 13). If the RF power does not provide adequate coverage of the tumor, the phase and amplitude of the array elements are adjusted and the process repeated until the coverage of the tumor is acceptable.

Another optimization technique involves the use of reduced gradient methods to provide the appropriate amplitude and phase of each element as well as temporal weighting. The actual SAR distribution may be evaluated through MR imaging as described above.

Once the array (1) has been tuned with optimized amplitudes, phases and weighting, the array can be switched to high power and directed in either a continuous or pulse mode, depending on the application, for the purpose of performing a hyperthermia treatment by heating the tumor to a temperature of, preferably, at least 42°–43° C. for at least 30–60 minutes (step 14). Temporal averaging allows the entire tumor to be fully heated to the therapeutic temperature.

During treatment, the temperature is preferably measured by periodically taking a rapid diffusion image and calculating temperature at each volume element in the patient (step 15). This provides a noninvasive method of monitoring the temperature. Diffusion imaging uses conventional imaging sequences plus additional gradients along the imaging plane axis. The signal attenuation that results can be related to the diffusion constant and therefore to the temperature.

Diffusion imaging techniques take on the order of seconds to carry out, and thus a full or a portion of such an image can be acquired without allowing the temperature of the tumor to drop below the desired temperature when the RF array (1) is turned off in order to perform this diffusion imaging. A plot of temperature isotherms may then be formed and superimposed directly on the MR image to provide a visual display of treatment progress.

Means are provided for compensating for bioheat transfer apparent from diffusion based temperature measurement. This will be accomplished through modification of the array parameters: element amplitude, phase and/or temporal weighting.

Figure 13:
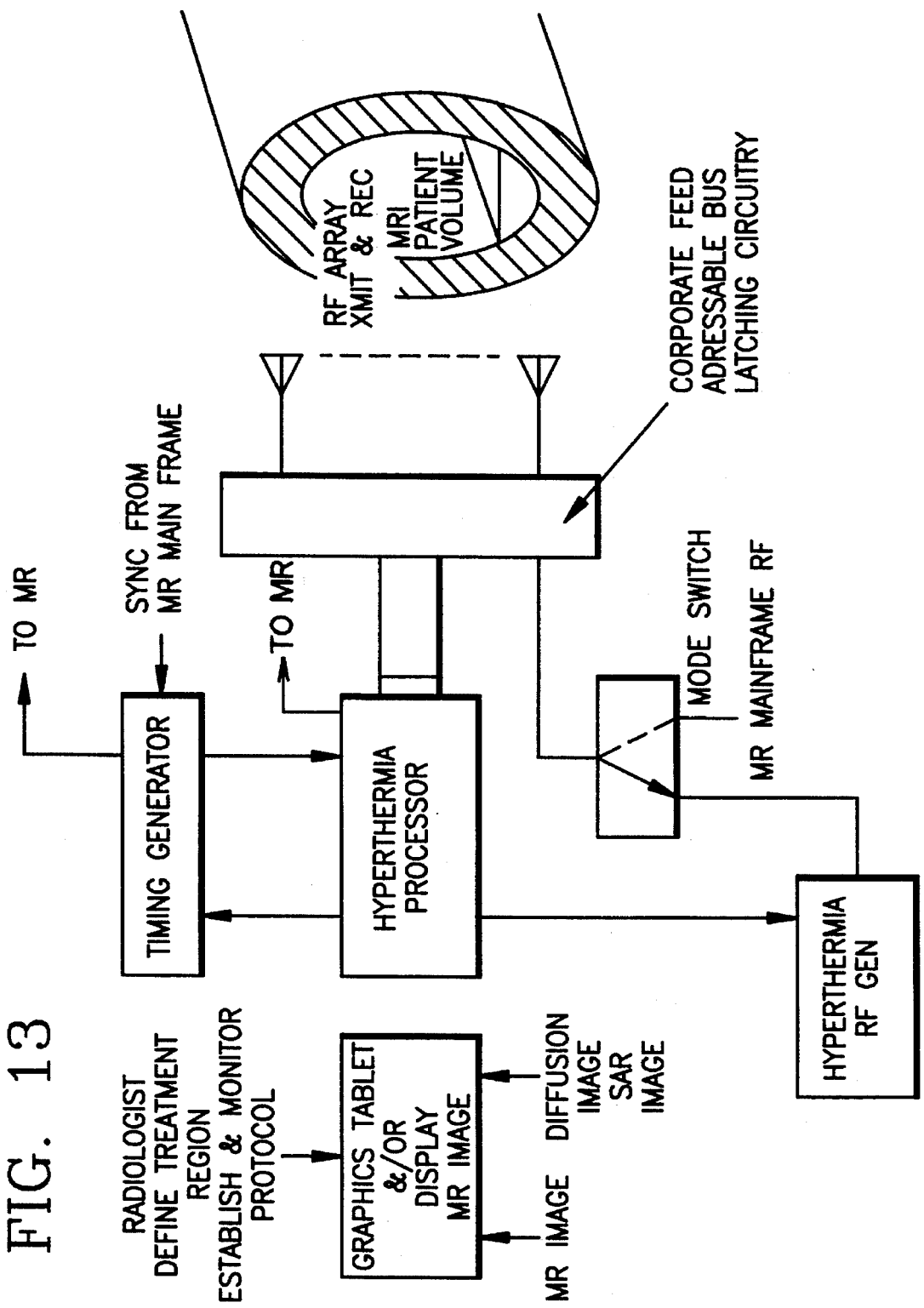
FIG. 13 is a block diagram of a preferred MR guided hyperthermia system.
Figure 14:
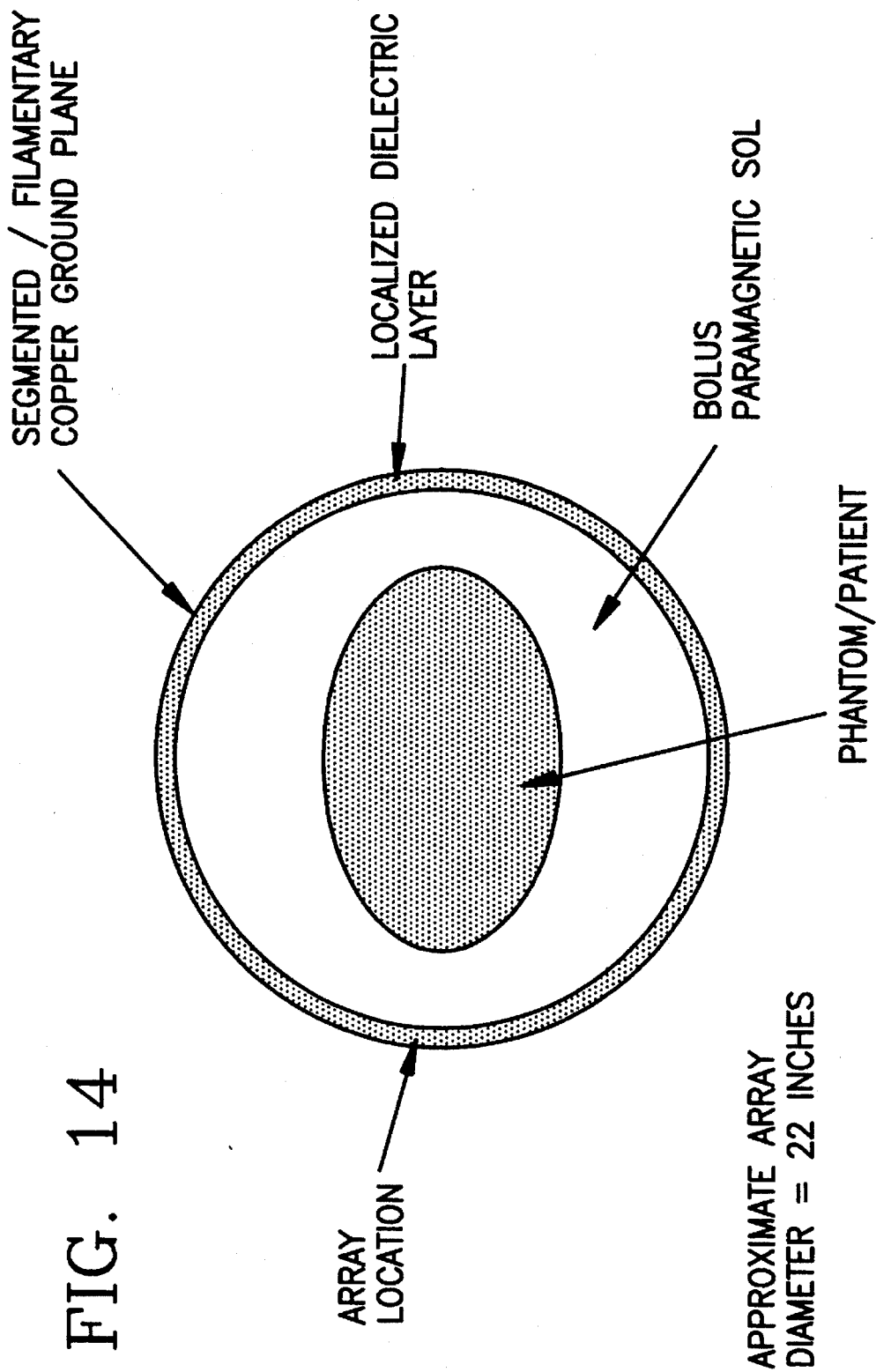
FIG. 14 is a cross-sectional view of the array used in FIG. 12.

A block diagram of a preferred MR-Guided Hyperthermia System apparatus is shown in FIG. 13. A conceptual cross-sectional view of a preferred array is shown in FIG. 14.

Although a specific embodiment of the invention has been described in connection with the drawing figures, it will be appreciated by those skilled in the art that a number of variations and modifications are possible within the scope of the invention. For example, imaging and heating need not be carried out at the same frequency. Temperature can be monitored by the MRI machine ($T_1$ measurement, fast spin-echo intensity, etc.) in addition to diffusion techniques. Higher or lower thermal doses can be employed for other therapies including ablation. Thus, it is intended that the invention not be limited in any way by the above description or accompanying drawings, but rather that it be defined solely by the appended claims.

We claim:

1. A system for hyperthermia treatment comprising:

an MR imaging machine having a proton MR imaging frequency for generating an MR image of a patient;

means including an RF phased antenna array positioned within the MR imaging machine for directing radio frequency (RF) radiation, at a frequency substantially equal to the proton MRI frequency, to a pathology in the patient situated within the MRI machine in order to non-invasively generate a specific absorption ratio (SAR) map of the patient for use in optimizing a subsequent application of RF power by the array during a hyperthermia treatment;

means including processors and controllers for controlling the RF phased array in concert with the MR imaging machine to provide the hyperthermia treatment;

means for noninvasively monitoring a temperature of said tumor and surrounding tissues upon evaluation of the tumor temperature in response to exposure to said radiation during the hyperthermia treatment; and means for dynamically controlling the RF power delivered to the target treatment area during the treatment based on said temperature monitoring means and said SAR map.

2. Apparatus as claimed in claim 1, wherein said temperature monitoring means comprises means for forming a rapid diffusion image of a patient using the MRI machine.

3. Apparatus as claimed in claim 1, wherein said RF phased array comprises a plurality of antenna elements.

4. Apparatus as claimed in claim 3, further comprising means for individually adjusting a phase and amplitude of each of said antenna elements.

5. Apparatus as claimed in claim 4, further comprising means for forming a visual display of said SAR map of radiation emitted by said antenna elements for comparison with said MR image of the patient in order to predict adjustments of the antenna elements which will provide for optimum coverage of the tumor.

6. Apparatus as claimed in claim 5, further comprising means for determining the optimum operating amplitude and phase of the antenna elements to provide for optimum coverage of the tumor.

7. Apparatus as claimed in claim 3, wherein said antenna elements are polarized parallel to a cylinder axis of the MRI machine.

8. Apparatus as claimed in claim 1, further comprising means for supplying a temporally averaged energy distribution of said radiation to improve localization in tumor.

9. Apparatus for hyperthermia treatment, comprising:

an MRI machine having an MR imaging resonant frequency for generating an MR image of a patient;

means including an RF phased array including a plurality of individually adjustable antenna elements positioned within the MRI machine for directing RF radiation having a frequency substantially equal to the resonant frequency at a tumor within the patient situated within the MRI machine;

means for supplying a temporally averaged energy distribution to said patient to improve localization of the tumor during a hyperthermia treatment; and means for determining and forming a visual display of an specific absorption ratio (SAR) distribution of radiation emitted by said antenna elements prior to the hyperthermia treatment for comparison with the MR image of the patient in order to predict adjustments of the antenna elements which will provide for optimum coverage of the tumor and thereby predict said temporally averaged energy distribution during the hyperthermia treatment.

10. Apparatus as claimed in claim 9, wherein said antenna elements are polarized parallel to a cylinder axis of the MRI machine.

11. Apparatus for hyperthermia treatment, comprising:

an MRI machine having an MR imaging resonant frequency for generating an MR image of a patient;

means including an RF phased array including a plurality of individually adjustable antenna elements positioned within the MRI machine for directing RF radiation having a frequency substantially equal to the resonant frequency at a tumor within the patient situated within the MRI machine; and means for determining and forming a visual display of an specific absorption ratio (SAR) distribution of radiation emitted by said antenna elements for comparison with the MR image of the patient in order to predict adjustments of the antenna elements which will provide for maximum coverage of the tumor during a subsequent hyperthermia treatment, said SAR distribution being obtained by measuring current distributions resulting from emission of said radiation by said antenna elements prior to the treatment.

12. Apparatus as claimed in claim 11, wherein said antenna elements are polarized parallel to a cylinder axis of the MRI machine.

13. A method of treatment, comprising the steps of:

placing a patient in a MRI machine including bolus/treatment array and taking a conventional MRI image;

using an RF phased array in said bolus/treatment array to generate a specific absorption ratio (SAR) map image to permit obtaining appropriate phase, amplitude, and temporal averaging; and superimposing the conventional and SAR map images and adjusting the phase and amplitude settings if necessary to obtain congruence between the images; and subsequently applying RF radiation from the phased array to heat the tumor.

14. A method as claimed in claim 13, wherein the step of applying RF radiation comprises the step of applying energy which is temporally averaged to improve localization in tumor.

15. A method as claimed in claim 14, wherein the step of applying the RF radiation comprises the step of keeping the tumor at approximately 42°–43° C. for 30–60 minutes.

16. A method as claimed in claim 13, further comprising the step of, periodically during the step of applying RF radiation for heating, obtaining a rapid diffusion image in order to monitor temperatures of said tumor and surrounding tissues.

17. A method of hyperthermia treatment, comprising the steps of:

placing a patient in a bolus/treatment array situated in an MRI machine;

applying RF energy to the patient and measuring resulting current densities in order to generate an specific absorption ratio (SAR) map of the patient;

using the SAR map as a basis for temporally averaging radiation to be applied to the patient during a hyperthermia treatment; and providing the hyperthermia treatment by applying the temporally averaged RF radiation to the patient in order to heat a tumor in the patient to a predetermined temperature for a predetermined period of time.

18. A method as claimed in claim 17, further comprising the step of, periodically, during the step of applying RF radiation by heating, obtaining a rapid diffusion image in order to monitor temperatures of said tumor and surrounding tissues.

19. A method as claimed in claim 17, wherein the step of applying the RF radiation comprises the step of keeping the tumor at approximately 42°–43° C. for 30–60 minutes.

* * * * *